United States Patent [19]

McCue

[11] Patent Number: 6,083,994

[45] Date of Patent: Jul. 4, 2000

[54] AQUEOUS BACTERICIDAL COMPOSITIONS BASED ON SYNERGISTIC COMBINATION OF LINEAR ALKYLBENZENESULFONATES AND N-PROPANOL

[75] Inventor: Karen Ann McCue, Tenafly, N.J.

[73] Assignee: Reckitt Benckiser Inc., Wayne, N.J.

[21] Appl. No.: 09/187,163

[22] Filed: Nov. 6, 1998

[30] Foreign Application Priority Data

Nov. 28, 1997 [GB] United Kingdom .................. 9725095

[51] Int. Cl.[7] .................................................. A01N 41/10
[52] U.S. Cl. ............................................ 514/709; 514/711
[58] Field of Search ..................... 514/578, 709, 514/711

[56] References Cited

U.S. PATENT DOCUMENTS 5,122,541  6/1992  Eggensperger et al. ................. 514/578

FOREIGN PATENT DOCUMENTS 9317723  9/1993  WIPO .............................. A61L 2/18
WO93/17723  9/1993  WIPO .............................. A61L 2/18

OTHER PUBLICATIONS

Copy of "Studies on Sodium Dodecyl Benzene Sulphonate in the Presence of Additives", Tenside, Surfactants, Detergents, vol. 35, No. 2, Mar., Apr. 1998, pp. 134–141, XP002096141.

Copy of PCT International Search Report for PCT/US98/23865 dated Apr. 22, 1999.

*Primary Examiner*—Jose' G. Dees
*Assistant Examiner*—Alton Pryor
*Attorney, Agent, or Firm*—Fish & Richardson P.C.

[57] ABSTRACT

Aqueous compositions comprising a synergistic combination of n-propyl alcohol and linear alkylbenzenesulfonate, especially dodecyl benzene sulfonate which provides good germicidal efficacy against both gram positive and gram negative bacteria on hard surfaces and the like. Processes for the sanitization of hard surfaces wherein the presence of gram positive and/or negative bacteria is suspected, is also disclosed.

6 Claims, No Drawings

AQUEOUS BACTERICIDAL COMPOSITIONS BASED ON SYNERGISTIC COMBINATION OF LINEAR ALKYLBENZENESULFONATES AND N-PROPANOL

The present invention relates to aqueous bactericidal compositions based on a synergistic combination of anionic surfactants and alcohols. These compositions find use in variety of applications for the sanitization of surfaces and articles wherein the presence of bacteria is suspected. The compositions also find use in cleaning and disinfecting compositions.

Known to the art are formulations in U.S. Pat. No. 5,122,541 which describes certain aqueous sprayable surface disinfectant compositions which include 20–30% by weight of a mixture of ethyl alcohol and isopropyl alcohol in a weight ratio of 1:2–2:1, and 0.05 to 0.5% wt of a mixture of anionic surfactants of the sulfonate or sulfate type, wherein the compositions are maintained in at a pH in the range of from about 2 to about 6, or about 8 to about 12.

While this and other prior art compositions are advantageous in certain respects, there remains a continuing need in the art for further improved formulations which provide a useful germicidal effect, especially those useful in the sanitization of hard surfaces and the like.

Accordingly it is an object of the invention to provide an aqueous liquid disinfectant composition which is particularly useful in the disinfection of surfaces wherein the presence of gram positive type pathogenic bacteria such as *Salmonella aureus,* and/or the presence of gram negative type pathogenic bacteria such as *Staphylococcus cholerasuis* is suspected.

Accordingly, a further object of the invention is a process for the disinfection of surfaces, especially hard surfaces, wherein the presence of gram positive type pathogenic bacteria and/or gram positive type pathogenic bacteria are suspected.

It is a still further object of the invention to provide a fast acting, liquid disinfectant composition useful for the disinfection of surfaces, especially hard surfaces wherein the presence of both gram positive type pathogenic bacteria and gram negative type pathogenic bacteria is suspected.

In accordance with the present invention, there has been found a synergistic combination of n-propyl alcohol and at least one linear alkylbenzenesulfonate which provides good germicidal efficacy against both gram positive and gram negative bacteria on hard surfaces and the like, which may be readily added to form part of an aqueous based composition. Desirably the total amount of n-propyl alcohol present is at least about 5% wt., more desirably in an amount of at least about 10% by weight, and may be present in greater amounts, based on the total weight of the composition of which it forms a part. Desirably the linear alkylbenzenesulfonate is present in an amount of at least about 0.05% wt., more preferably is present in an amount of at least about 0.5% wt., more preferably is present in an amount of at least about 1% wt., and still more preferably in an amount of at least about 2% wt., based on the total weight of the composition having 100% wt. of which it forms a part.

Most desirably the linear alkylbenzenesulfonate is dodecyl benzene sulfonate.

Such a result is surprising as it has been found that similar alcohols, even isopropanol, and similar surfactants do not provide the same type beneficial level of germicidal efficacy achieved with the synergistic combination which only the present inventor has discovered.

According to a preferred aspect of the invention, there is provided an aqueous sanitizing composition which includes n-propyl alcohol and dodecyl benzene sulfonate as described above, wherein said sanitizing composition is useful against both gram positive and gram negative bacteria. In accordance with a further aspect of the invention, there is provided such an aqueous sanitizing composition which is fast acting, particularly as demonstrated by the examples discussed below. Both the n-propyl alcohol and the dodecyl benzene sulfonate are commercially available. The n-propyl alcohol is available from a variety of sources; the dodecyl benzene sulfonate is commercially available as a salt form in a surfactant preparation marketed under the tradename Calsoft® L-60 which is described to be a sodium dodecyl benzene sulfonate.

In accordance with certain particularly preferred embodiments, there is provided an aqueous sanitizing composition wherein is present a linear alkylbenzenesulfonate in an amount of from 0.05–2% wt., and more preferably is a salt of dodecyl benzene sulfonate, especially sodium dodecyl benzene sulfonate and n-propanol which is present in an amount of 7.5–10% wt. based on the total weight of the composition of which these two constituents form a part.

The aqueous compositions according to the invention, in addition to n-propyl alcohol and dodecyl benzene sulfonate mixture denoted above, may further include one or more conventional constituents including but not limited to: further non-aqueous solvents, chelators, building agents, pH buffering agents, perfumes, perfume carriers, stabilizing agents, coloring agents, hydrotropes, antifoaming agents, as well as one or more nonionic, cationic, anionic, amphoteric or zwitterionic surfactants; one or more of these may be included in any amount which do no undesirably detract from the antimicrobial activity of the compositions. Such materials are known to the art, including those described in *McCutcheon's Emulsifiers and Detergents* (Vol. 1), *McCutcheon's Functional Materials* (Vol. 2), North American Edition, 1991; *Kirk-Othmer, Encyclopedia of Chemical Technology,* 3rd Ed., Vol. 22, the contents of which are herein incorporated by reference For any particular composition, such optional ingredients should be compatible with the other ingredients present.

It is to be understood also, that the aqueous compositions according to the invention also include, or may consist essentially of, the n-propyl alcohol and one or more linear alkylbenzensulfonates, particularly the most preferred dodecyl benzene sulfonates and water, without further conventional constituents. In a further alternative, inventive compositions include, or may consist essentially of the n-propyl alcohol and one or more linear alkylbenzensulfonates, particularly the most preferred dodecyl benzene sulfonates and water, optionally further with one or more conventional constituents but excluding surfactants.

It is further to be understood that the dodecyl benzene sulfonate according to the invention may be used in either its free acid form or as a salt form, where such salts include alkali metal and alkaline earth metal salts, and especially sodium, potassium and chlorine.

A particular advantage of the inventive compositions is the fact that in preferred embodiments, they comprise relatively low amounts of volatile organic constituents. Of increasing interest are the provision of products which satisfy the stringent requirements of the US Environmental Protection Agency for low volatile organic content ("low VOC") products. According to specific preferred embodiments the ready to use disinfecting compositions provided herein meet such stringent requirements.

The inventive compositions may be used in a wide variety of disinfecting applications and in a wide variety of environments which may benefit from a disinfecting effect. These applications and environments include usage in the medical sector for the disinfection of instruments and apparatuses, as well as for disinfection or decontamination of operating theaters and fixtures therein. The use of the compositions for the disinfection or decontamination of hospital environments specifically include: lavatories and lavatory fixtures hospitals, clinics, examining rooms, and other environments associated with the provision of healthcare services and wherein the presence of gram positive bacteria and/or gram negative bacteria are suspected is also expressly contemplated. Such environments are to be understood to include not only the surfaces of walls, ceilings and floors, but to specifically include other surfaces such as the surfaces of various health care apparatus which may be found in such environments wherein healthcare surfaces are provided. The use of the inventive compositions provides an effective and simple to use method for the disinfection of such environments.

The inventive compositions are particularly to be understood to include hard surfaces. By way of non-limiting example, hard surfaces suitable for coating with the polymer include surfaces composed of refractory materials such as: glazed and unglazed tile, brick, porcelain, ceramics as well as stone including marble, granite, and other stones surfaces; glass; metals; plastics e.g. polyester, vinyl; fiberglass, Formica®, Corian® and other hard surfaces known to the industry. Hard surfaces which are to be particularly denoted are lavatory fixtures such as shower stalls, bathtubs and bathing appliances (racks, curtains, shower doors, shower bars) toilets, bidets, wall and flooring surfaces especially those which include refractory materials and the like. Further hard surfaces which are to be denoted are those associated with kitchen environments and other environments associated with food preparation, including cabinets and countertop surfaces as well as walls and floor surfaces especially those which include refractory materials, plastics, Fiberglass®, Formica®, Corian® and stone.

The compositions according to the invention can be desirably provided as a ready to use product in a manually operated spray dispensing container. Such a typical container is generally made of synthetic polymer plastic material such as polyethylene, polypropylene, polyvinyl chloride or the like and includes spray nozzle, a dip tube and associated pump dispensing parts and is thus ideally suited for use in a consumer "spray and wipe" application. In such an application, the consumer generally applies an effective amount of the composition using the pump and a short time thereafter, wipes off the treated area with a rag, towel, or sponge, or other material. In this manner, disinfection of the treated surface may be achieved.

In a yet a further embodiment, the compositions according to the invention may be formulated so that it may be useful in conjunction with a "aerosol" type product wherein it is discharged from a pressurized aerosol container. Known art propellants such as liquid propellants based on chloroflurocarbons or propellants of the non-liquid form, i.e., pressurized gases, including carbon dioxide, air, nitrogen, as well as others, may be used, even though it is realized that the former chlorofluorocarbons are not generally further used due to environmental considerations. In such an application, a composition according to the invention is dispensed by activating the release nozzle of said aerosol type container onto a surface in need of disinfection, and generally in accordance with a manner as above-described is removed with the use of a rag, towel, or sponge, or other material.

It is to be understood that the compositions according to the invention may be applied to a surface which is in need of disinfection, particularly where the presence of gram positive and/or gram negative bacteria are suspected.

In particularly preferred embodiments the compositions according to the invention provide at least a log 2 reduction using a Microbial Reduction Assay against either *Salmonella choleraesuis* (gram negative type pathogenic bacteria) and *Staphylococcus aureus* (gram positive type pathogenic bacteria) for a 5 minute contact time, and more preferably for a 1 minute contact time. Preferably, the preferred embodiments of the inventive compositions are effective against both either *Salmonella choleraesuis* (gram negative type pathogenic bacteria) and *Staphylococcus aureus* (gram positive type pathogenic bacteria) for a 5 minute contact time, and more preferably for a 1 minute contact time.

According to further particularly preferred embodiments there are provided compositions according to the invention which consist essentially of from 0.05–2% wt of a linear alkylbenzenesulfonate, especially a salt of dodecyl benzene sulfonate, especially sodium dodecyl benzene sulfonate, 7.5–1 0% wt. of n-propanol, with the remaining balance to 100% wt. being water, wherein such composition provides at least a log 2 reduction using a Microbial Reduction Assay against either *Salmonella choleraesuis* (gram negative type pathogenic bacteria) and *Staphylococcus aureus* (gram positive type pathogenic bacteria) for a 5 minute contact time. In particularly preferred embodiments, the inventive compositions are effective against both either *Salmonella choleraesuis* (gram negative type pathogenic bacteria) and *Staphylococcus aureus* (gram positive type pathogenic bacteria) for a 5 minute contact time, and more preferably for a 1 minute contact time.

One skilled in the art will recognize that modifications may be made in the present invention without deviating from the spirit or scope of the invention. The invention is illustrated further by the following examples which are not to be construed as limiting the invention or scope of the specific procedures described herein.

EXAMPLES

For purposes of illustration of the present inventive compositions, various formulations were produced and are reported below; comparative formulations are illustrated on Table 1, while formulations according to the invention are described in Table 2 below. These formulations were produced generally in accordance with the following protocol.

Into a suitably sized vessel, a measured amount of room temperature water (approx. 68° F., 20° C.) was provided after which measured amounts of remaining constituents were added. All of the remaining constituents were similarly supplied at room temperature; mixing of the constituents was achieved by the use of a magnetic stirrer apparatus. Mixing, which generally lasted several minutes, and maintained until the particular exemplary formulation appeared to be homogeneous.

It is to be noted that the constituents might be added in any order, but it is preferred that water be the initial constituent provided to a mixing vessel or apparatus as it is the major constituent and addition of the further constituents thereto is convenient.

The exact compositions of the example formulations are listed on Table 1; the weights given are the "as is" weight of materials as supplied by their respective supplier, and unless otherwise indicated, the weight percents of the active portion of each of the constituents are to be understood to represent 100% by weight.

TABLE 1

|  | C1 | C2 | C3 | C4 | C5 | C6 | C7 | C8 | C9 | C10 | C11 | C12 | C13 | C14 | C15 |
|---|---|---|---|---|---|---|---|---|---|---|---|---|---|---|---|
| Ethanol | — | 10.0 | — | — | 10 | 5.0 | 10 | 10 | — | — | — | — | — | — | — |
| isopropanol | — | — | — | — | — | — | — | — | — | — | — | 10.0 | — | — | — |
| Dowanol DB | — | — | — | — | — | — | — | — | — | — | — | — | 5.0 | — | — |
| n-propanol | 10.0 | — | — | — | — | — | — | — | 5.0 | 5.0 | — | — | — | 10.0 | 10.0 |
| Hostapur SAS | — | — | — | — | — | — | 2.0 | — | — | — | — | — | — | 2.0 | — |
| Standapol SLS | — | — | — | — | — | — | — | 1.0 | — | — | — | — | — | — | 2.0 |
| Biosoft D-40 | — | — | 0.1 | — | — | — | — | — | — | — | — | — | — | — | — |
| Calsoft L-60 | — | — | — | 2.0 | 2.0 | 2.0 | — | — | — | 0.05 | — | 2.0 | 2.0 | — | — |
| water | q.s. | q.s. | q.s. | q.s. | q.s. | q.s. | q.s. | q.s. | q.s. | q.s. | q.s. | q.s. | q.s. | q.s | q.s. |
| # of Log10 reduction |  |  |  |  |  |  |  |  |  |  |  |  |  |  |  |
| 1 Minute: |  |  |  |  |  |  |  |  |  |  |  |  |  |  |  |
| S. cholerasuis | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| S. aureus | 0.0 | 0.0 | 2.8 | 2.6 | 2.6 | 2.3 | 2.9 | 3.5 | 0.0 | 1.8 | 3.6 | 3.5 | 1.1 | 3.5 | 3.5 |
| 5 Minutes: |  |  |  |  |  |  |  |  |  |  |  |  |  |  |  |
| S. cholerasuis | 4.4 | 0.0 | 0.0 | 0.0 | 0.0 | 0.0 | 3.2 | 0.0 | 0.0 | 0.0 | 2.2 | 1.0 | 0.0 | 0.0 | 1.4 |
| S. aureus | 0.0 | 0.0 | 3.3 | 3.9 | 3.9 | 2.3 | 3.8 | 3.9 | 0.1 | 2.3 | 4.4 | 4.1 | 1.0 | 4.5 | 6.3 |

Dowanol DB is diethylene glycol n-butyl ether (Dow Chemical Co.)
Hostapur SAS is a sodium secondary alkane sulfonate (60% wt. actives) (Hoechst AG)
Standapol SAS is a sodium lauryl sulfonate (_% wt. actives) (Henkel Corp.)
Biosoft D-40 is a sodium linear alkylate sulfonate (40% wt. actives) (Stepan Co.)
Calsoft L-60 is sodium salt of an dodecyl benzene sulfonate (60% wt. actives) (Pilot Chemical Co.)

TABLE 2

|  | E1 | E2 | E3 | E4 | E5 | E6 | E7 | E8 |
|---|---|---|---|---|---|---|---|---|
| ethanol | — | — | — | — | — | — | — | — |
| isopropanol | — | — | — | — | — | — | — | — |
| Dowanol DB | — | — | — | — | — | — | — | — |
| n-propanol | 10 | 10 | 10 | 10 | 10 | 10 | 10 | 7.5 |
| Hostapur SAS | — | — | — | — | — | — | — | — |
| Standapol SLS | — | — | — | — | — | — | — | — |
| Biosoft D-40 | — | — | — | — | — | — | — | — |
| Calsoft L-60 | 2 | 2 | 2 | 0.5 | 0.5 | 0.06 | 0.05 | 2 |
| water | q.s. | q.s. | q.s. | q.s. | q.s. | q.s. | q.s. | q.s. |
| # of Log10 reduction |  |  |  |  |  |  |  |  |
| 1 Minute: |  |  |  |  |  |  |  |  |
| S. cholerasuis | 4.7 | 5.8 | 4.7 | 6.7 | 5.3 | 6.7 | 4.9 | 4.9 |
| S. aureus | 5.2 | 3.4 | 3.6 | 3.3 | 3.3 | 3.1 | 2.9 | 2.9 |
| 5 Minutes: |  |  |  |  |  |  |  |  |
| S. cholerasuis | 4.9 | 5.6 | 4.4 | 6.9 | 6.9 | 6.9 | 4.3 | 4.3 |
| S. aureus | 5.0 | 4.2 | 4.2 | 3.5 | 3.3 | 3.6 | 3.5 | 3.5 |

Dowanol DB is diethylene glycol n-butyl ether (Dow Chemical Co.)
Hostapur SAS is a sodium secondary alkane sulfonate (60% wt. actives) (Hoechst AG)
Standapol SAS is a sodium lauryl sulfonate (_% wt. actives) (Henkel Corp.)
Biosoft D-40 is a sodium linear alkylate sulfonate (40% wt. actives) (Stepan Co.)
Calsoft L-60 is sodium salt of an dodecyl benzene sulfonate (60% wt. actives) (Pilot Chemical Co.)

The sanitizing efficacy of the inventive compositions were determined as follows:

Formulations described on Tables 1 and 2 above, were evaluated for antimicrobial efficacy at a dilution of 1:500 using a Microbial Reduction Assay against *Salmonella choleraesuis* (gram negative type pathogenic bacteria) and *Staphylococcus aureus* (gram positive type pathogenic bacteria). The test protocol followed for each sample was generally as follows.

1. Inoculation of the Samples
   A. Inoculate 1.0 ml of the 24 hour test culture into each 9.0 ml sample tube; and test in duplicate.
   B. Subculture 1.0 ml of the sample after 1 or 5 minutes contact time with the respective diluted Example formulation.
   C. Subculture the sample into 9.0 ml of DIFCO AOAC Letheen Broth to form a "$10^{-1}$ Sample" dilution.
2. Sample Dilutions and Plating
   A. Plate the $10^{-1}$, $10^{-3}$, and $10^{-5}$ dilutions for each sample/organism/contact time combination by the following general protocol:
      1. From the $10^{-1}$ "Sample" dilution, plate 1.0 ml to form a $10^{-1}$ "Sample" plate.
      2. Pipette and transfer 0.1 ml of the $10^{-1}$ Sample dilution into 9.9 ml of DIFCO AOAC Letheen Broth to form a "$10^{-3}$ Sample" dilution and form a $10^{-3}$ plate.
      3. Pipette and transfer 0.1 ml of $10^{-3}$ Sample dilution to 9.9 ml DIFCO AOAC Letheen Broth to form a "$10^{-5}$ Sample" dilution and form a $10^{-5}$ plate.
   B. Pour each of the $10^{-1}$ plates, $10^{-3}$ plate, and $10^{-5}$ plate with Tryptic Soy Agar containing polysorbate 80 and lecithin (either DIFCO or BBL).
   C. Incubate the plates for 48 hours at 35° C.
3. Control Counts: Dilutions and Plating
   A. Inoculate 1.0 ml of 24 hour test culture into 9.0 ml DIFCO AOAC Letheen Broth to form a "Control" dilution.
   B. Subculture 1.0 ml of the Control dilution into 9.0 ml DIFCO AOAC Letheen Broth at 1 and at a 5 minute exposure; these are the "$10^{-1}$ Control" dilution tubes for the 1 and 5 minute contact time controls.
   C. Plate $10^{-4}$ and $10^{-5}$ dilutions of the $10^{-1}$ Control dilution for each contact time by the following protocol:
      1. Pipette 0.1 ml of the $10^{-1}$ Control dilution into 9.9 ml DIFCO AOAC Letheen Broth to form a "$10^{-3}$ Control" dilution.
      2. Plate 1.0 ml of the $10^{-3}$ Control dilution into 9.0 ml DIFCO AOAC Letheen Broth to form a "$10^{-4}$ Control" dilution and form a $10^{-4}$ Control" plate.
      3. Pipette 0.1 ml of the $10^{-3}$ Control dilution into 9.9 ml of ml DIFCO AOAC Letheen Broth to form a "$10^{-5}$ Control" dilution, and to form a $10^{-5}$ Control" plate.

4. Pour the $10^{-4}$ and $10^{-5}$ Control plates with Tryptic Soy Agar containing polysorbate 80 and lecithin, and incubate at 35° C. for 48 hr.

4. Calculation of $Log_{10}$ Reduction

A. Determine the number of bacteria survivors at each contact time for both the controls and test samples of each of the plates produced in accordance with the protocols outlined for steps 1–3 denoted above.

1. Count the number of colonies on the petri dish. The plate is acceptable for counting with a colony count between 25 and 250.
2. Multiply the number of colonies by the plate dilution factor=the number of surviving bacteria/ml.

B. Determine the numbers of $Log_{10}$ reduction in bacteria for each sample/organism/contact time combination in accordance with the following equation:

$Log_{10}$ (Control Count)–$Log_{10}$ (Survivor Count)=#$Log_{10}$ of bacteria reduction For this test with a contact time of 1 minute and 5 minutes, a $Log_{10}$ reduction value of 3 or greater against both organisms is acceptable for "passing" performance (i.e., broad spectrum antimicrobial activity), any lesser $Log_{10}$ reduction value indicates unacceptably poor antimicrobial efficacy. The results of this evaluation are summarized on Tables 1 and 2, above, as indicated with respect to the particular formulation being evaluated.

As may be seen from the results indicated, the formulations of Table 2 consistently provided superior antimicrobial performance against both gram positive and gram negative pathogenic bacteria. This result is surprising as results of a 10% wt. aqueous dilution of n-propanol (C1) are somewhat effective against *S. cholerasuis* but only at a 5 minute contact time, but have no effect against *S. aureus*. Conversely a 2% wt. aqueous dilution of the sodium salt of an dodecyl benzene sulfonate(C4) is somewhat effective against *S. aureus*, at both 1 and 5 minute contact times, but has no effect against *S. cholerasuis*. Compositions within the scope of the present invention, non-limiting examples of which are illustrated on Table 2 show much higher efficacy levels against both *S. aureus*, and *S. cholerasuis*, and at the same time, at much shorter contact times. Such superior results are surprising and unexpected.

Several of the exemplary formulations described in more detail on Table 1 and Table 2 above were further evaluated in order to evaluate their antimicrobial efficacy against *Salmonella choleraesuis* (gram negative type pathogenic bacteria) (ATCC 10708). The testing was performed in accordance with the protocols outlined in "Use-Dilution Method", Protocols 955.14, 955.15 and 964.02 described in Chapter 6 of "Official Methods of Analysis", $16^{th}$ Edition, of the Association of Official Analytical Chemists; the contents of which are herein incorporated by reference. This test is also commonly referred to as the "AOAC Use-Dilution Test Method".

As is appreciated by the skilled practitioner in the art, the results of the AOAC Use-Dilution Test Method indicates the number of test substrates wherein the tested organism remains viable after contact for 10 minutes with at test disinfecting composition /total number of tested substrates (cylinders) evaluated in accordance with the AOAC Use-Dilution Test. Thus, a result of "0/40" indicates that of 60 test substrates bearing the test organism and contacted for 10 minutes in a test disinfecting composition, 0 test substrates had viable (live) test organisms at the conclusion of the test. Such a result is excellent, illustrating the excellent disinfecting efficacy of the tested composition.

Results of the antimicrobial testing are indicated on Table 3, below. The reported results indicate the number of test cylinders with live test organisms/number of test cylinders tested for each example formulation and organism tested.

TABLE 3

| Antimicrobial Efficacy (AOAC Test Method) | |
| --- | --- |
| Formulation: | *Salmonella choleraesuis* |
| C1 | 12/40 |
| E2 | 0/40 |

As may be seen from the results indicated above, the compositions according to the invention provide excellent antimicrobial efficacy of these compositions against known bacteria commonly found in bathroom, kitchen and other environments.

As may be readily determined by inspection of the results obtained and reported in Tables 1 and 2, the dodecyl benzene sulfonate surfactant, specifically the Calsoft T-60 surfactant preparation, in conjunction with the n-propanol surprisingly provided superior disinfecting efficacy as compared to combinations of other sulfate or sulfonate based surfactant compounds, as well as with other alcohols or glycol ether solvents.

While the invention is susceptible of various modifications and alternative forms, it is to be understood that specific embodiments thereof have been shown by way of example in the drawings which are not intended to limit the invention to the particular forms disclosed; on the contrary the intention is to cover all modifications, equivalents and alternatives falling within the scope and spirit of the invention as expressed in the appended claims.

What is claimed is:

1. An aqueous hard surface sanitizing composition which comprises:

7.5–10% wt. of n-propyl alcohol and 0.05–2% wt. of dodecyl benzene sulfonate, wherein said sanitizing composition provides at least a log 2 reduction using a Microbial Reduction Assay against *Salmonella choleraesuis* or *Staphylococcus aureus* for a 5 minute contact time.

2. An aqueous hard surface sanitizing composition according to claim 1 which comprises:

7.5–10% wt. of n-propyl alcohol and 0.05–2% wt. of dodecyl benzene sulfonate, wherein said sanitizing composition provides at least a log 2 reduction using a Microbial Reduction Assay against *Salmonella choleraesuis* and *Staphylococcus aureus* for a 1 minute contact time.

3. An aqueous hard surface sanitizing composition according to claim 1 which consists essentially of:

7.5–10% wt. of n-propyl alcohol and 0.05–2% wt. of dodecyl benzene sulfonate, to 100% wt. water, wherein said sanitizing composition provides at least a log 2 reduction using a Microbial Reduction Assay against *Salmonella choleraesuis* or *Staphylococcus aureus* for a 5 minute contact time.

4. An aqueous hard surface sanitizing composition according to claim 3 which consists essentially of:

7.5–10% wt. of n-propyl alcohol and 0.05–2% wt. of dodecyl benzene sulfonate, to 100% wt. water, wherein said sanitizing composition provides at least a log 2 reduction using a Microbial Reduction Assay against

*Salmonella choleraesuis* or *Staphylococcus aureus* for a 1 minute contact time.

5. A process for the sanitization of surfaces and articles wherein the presence of bacteria is suspected which comprises the process step of:

contacting the surface with a disinfecting effective amount of a composition according to claim 1 for a sufficient time to sanitize said surface.

6. A process for the sanitization of surfaces and articles wherein the presence of bacteria is suspected which comprises the process step of:

contacting the surface with a disinfecting effective amount of a composition according to claim 3 for a sufficient time to sanitize said surface.

* * * * *

UNITED STATES PATENT AND TRADEMARK OFFICE
CERTIFICATE OF CORRECTION

PATENT NO. : 6,083,994  
DATED : July 4, 2000  
INVENTOR(S) : Karen Ann McCue

Page 1 of 1

It is certified that error appears in the above-identified patent and that said Letters Patent is hereby corrected as shown below:

<u>Title page</u>,
Item [56], delete the following:

"9317723    9/1993    WIPO...............A61L 2/18"

and insert:

-- 0 601 452 A1 6/1994 EPO..........................A01N 31/02 --

Signed and Sealed this

Second Day of October, 2001

Attest:

NICHOLAS P. GODICI
*Attesting Officer*   *Acting Director of the United States Patent and Trademark Office*